United States Patent

Bonte et al.

Patent Number: 6,136,851
Date of Patent: Oct. 24, 2000

[54] TOCOPHEROL ESTERS AND THEIR COSMETIC AND PHARMACEUTICAL USES

[75] Inventors: Frédéric Bonte; Alex Saunois, both of Orleans, France

[73] Assignee: LVMH Recherche, Paris, France

[21] Appl. No.: 09/423,513

[22] PCT Filed: May 14, 1998

[86] PCT No.: PCT/FR98/00958

§ 371 Date: Nov. 10, 1999

§ 102(e) Date: Nov. 10, 1999

[87] PCT Pub. No.: WO98/51679

PCT Pub. Date: Nov. 19, 1998

[30] Foreign Application Priority Data

May 14, 1997 [FR] France ................................ 97 05907

[51] Int. Cl.[7] ...................... A61K 31/555; C07D 311/72
[52] U.S. Cl. .......................... 514/458; 424/60; 514/844; 549/410
[58] Field of Search .............. 549/410; 514/458, 514/844; 424/60

[56] References Cited

FOREIGN PATENT DOCUMENTS

| 2 314 722 | 1/1977 | France . |
| 24 39 139 | 2/1975 | Germany . |

*Primary Examiner*—Bernard Dentz
*Attorney, Agent, or Firm*—Nath & Associates PLLC; Gary M. Nath; Jerald L. Meyer

[57] ABSTRACT

The invention relates to an ester. The ester is characterized in that it presents the following chemical formula (I):

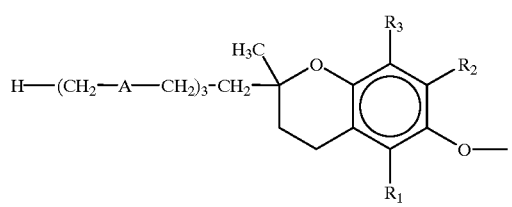

(I)

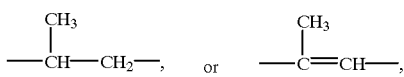

in which:
$R_1$, $R_2$ and $R_3$ independently represent an atom of hydrogen, a methyl radical,
A represents the following groups:

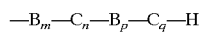

$R_4$ and $R_5$ are identical or different and each represents a chain of the form:

$$-B_m-C_n-B_p-C_q-H$$

in which:
B is the following group:

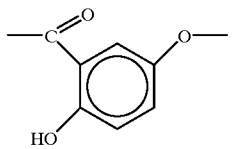

C is the following group:

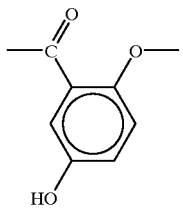

and in which the indices m, n, p, and q are respective integers lying in the range 0 to 4, it being understood that the sum m+n+p+q is limited to integers in the range 0 to 4.

The ester can be used for preparing cosmetic or pharmaceutical, in particular dermatological, compositions having activity against radicals, against inflammation, favoring differentiation of keratinocytes, improving skin moisturizing, improving skin grain fineness, and having anti-aging or depigmenting activity.

22 Claims, 1 Drawing Sheet

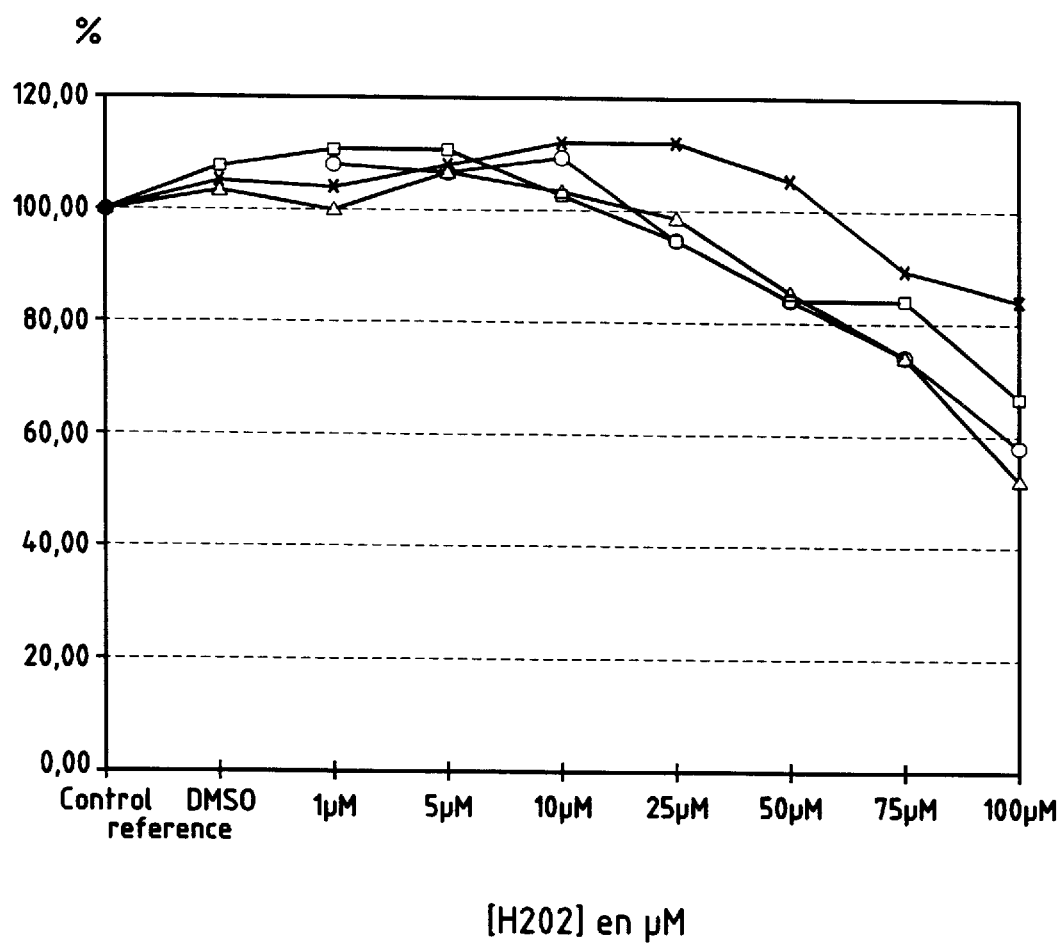

TOCOPHEROL ESTERS AND THEIR COSMETIC AND PHARMACEUTICAL USES

This application is a 371 of PCT/FR98/00958 filed May 14, 1998.

FIELD OF THE INVENTION

The invention relates by way of novel substance to tocopherol esters, to a use thereof in cosmetics or pharmacy, in particular dermatology, and also to cosmetic or pharmaceutical, and in particular dermatological, compositions containing them.

SUMMARY OF THE PRIOR ART

It is known that alpha-tocopherol or vitamin E is to be found in the natural state in numerous plants, usually with other compounds such as beta-tocopherol, gamma-tocopherol, and delta-tocopherol.

Alpha-tocopherol is essentially used to combat vitamin E deficiencies, or as a nutrient, in particular to combat muscular degeneration.

It is also used as an antioxidizing agent, but in highly specific doses.

SUMMARY OF THE INVENTION

In the context of the present invention, there have been discovered in a manner that is quite surprising and unexpected, both novel esters of tocopherol and the fact that these novel esters of tocopherol present powerful activity against radicals, against inflammation, in improving differentiation of keratinocytes, in improving moisturizing of the skin, in improving skin grain fineness, in anti-aging activity, in depigmenting activity, and in anesthetic effects on cutaneous nerve endings.

Thus, the present invention seeks to resolve the novel technical problem consisting in supplying an active substance having good activity against radicals, against inflammation, against aging, for depigmenting, for improving the differentiation of keratinocytes, for moisturizing the skin, for the fineness of skin grains, and also anesthetic action on cutaneous nerve endings, in particular by topical or general application, thus constituting an active ingredient that is valuable in preparing cosmetic, pharmaceutical, and in particular dermatological compositions.

The present invention resolves this novel technical problem in satisfactory manner using a solution that is particularly simple, and suitable for use on an industrial scale.

DETAILED DESCRIPTION OF THE INVENTION

Thus, in a first aspect, the present invention covers esters, characterized in that they present the following chemical formula (I):

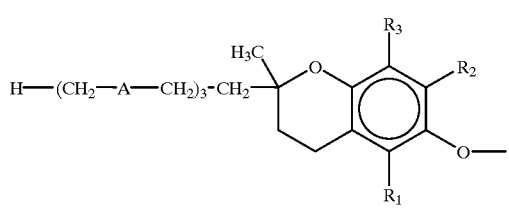
(I)

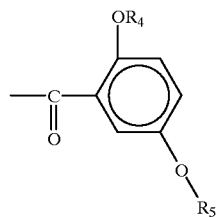

in which:

$R_1$, $R_2$ and $R_3$ independently represent an atom of hydrogen, a methyl radical, A represents the following groups:

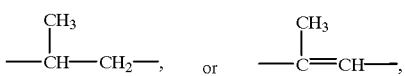

$R_4$ and $R_5$ are identical or different and each represents a chain of the form:

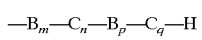

in which:

B is the following group:

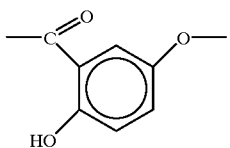

C is the following group:

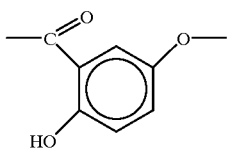

and in which the indices m, n, p, and q are respective integers lying in the range 0 to 4, it being understood that the sum m+n+p+q is limited to integers in the range 0 to 4.

In a variant embodiment of the invention, the esters are characterized in that $R_4$ and $R_5$ represent hydrogen.

In a variant embodiment of the invention, the esters are characterized in that at least one of the groups $R_4$ and $R_5$ represents hydrogen.

In a variant embodiment of the invention, the esters are characterized in that one of the groups $R_4$ or $R_5$ represents hydrogen, and the other a 2,5-dihydroxybenzoyl radical.

In a variant embodiment of the invention, the esters are characterized in that they are selected from the group consisting in esters of alpha-tocopherol, of beta-tocopherol, of gamma-tocopherol, of zeta 1-tocopherol, of zeta 2-tocopherol, of delta-tocopherol, of eta-tocopherol, of epsilon-tocopherol, and of tocol.

In a variant embodiment of the invention, it relates to an ester satisfying formula (II) below:

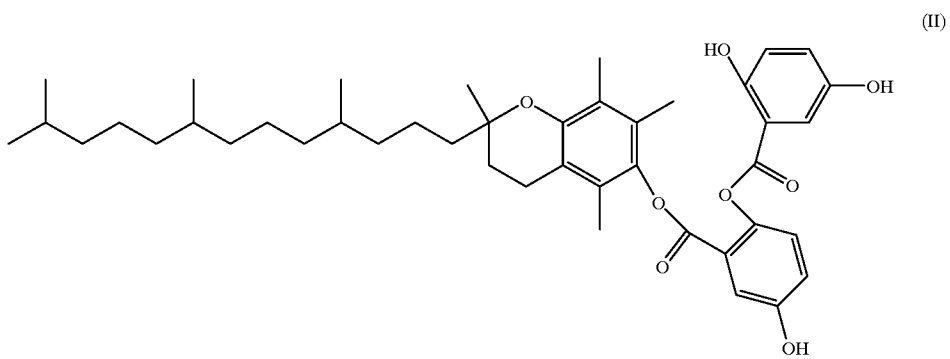

(II)

In a variant embodiment of the invention, it relates to an ester satisfying formula (III) below:

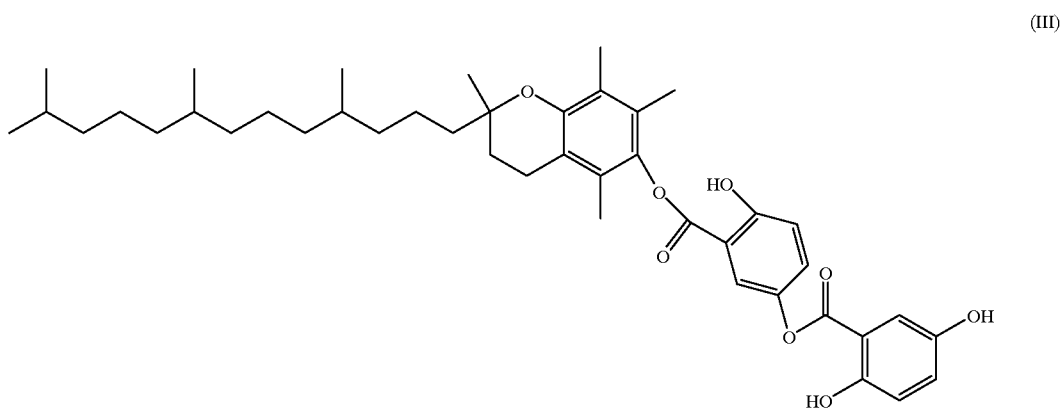

(III)

Esters of above formulae (II) and (III) are referred to below as alpha-tocopherol 2,5-dihydroxybenzoate diester respectively of formula (II) and of formula (III), or else as "diester $A_1$" and "diester $A_2$".

In a second aspect, the present invention also covers a cosmetic or pharmaceutical composition, and in particular a dermatological composition, characterized in that by way of active ingredient it comprises at least one ester of formula (I) as defined above.

In a variant embodiment, the said composition is characterized in that it comprises as active ingredient at least two esters as defined above, in the form of a mixture.

In a variant embodiment, the said composition is characterized in that the said ester is present in a fatty phase of said composition.

In another variant embodiment, the said composition is characterized in that the fatty phase comprises at least one cosmetically or pharmaceutically or dermatologically acceptable oil, in particular an oil selected from the group constituted by jojoba oil, macadamia oil, limnanthes seed oil, in particular from *Limnanthes alba benth* (Meadowfoam), mineral oils, and triglycerides, in particular triglycerides based on caprylic acid and/or capric acid, or mixtures thereof.

In a variant embodiment, the said composition is characterized in that its concentration in said formula I ester lies in the range 0.001% to 5%, better in the range 0.01% to 1% by weight relative to the total weight of the final composition.

In a particular variant embodiment, the said composition is characterized in that it comprises as an active ingredient at least one alpha-tocopherol ester corresponding to said chemical formula I, in which each of $R_1$, $R_2$ and $R_3$ represents a methyl radical, A represents the group:

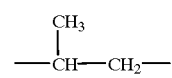

and $R_4$ and $R_5$ have the values as defined above.

In another variant embodiment, said composition is characterized in that it comprises at least one other active ingredient, in particular selected from the group constituted by vitamins A, B1, B6, B12, E, C, PP, retinoic acid, retinal, retinol and esters thereof, salicylic acid and derivatives thereof, in particular salts or esters thereof, 2,5-dihydroxybenzoic acid, tocopherol and esters thereof, in particular tocopherol phosphate, asiatic acid, madecassic acid and its glycoside-containing esters, asiaticoside, an extract of *Centella asiatica*, an extract of *Siegesbeckia orientalis*, proantocyanide oligomers, in particular those obtained from grape pips, and esters thereof, in particular the palmitic and stearic esters, derivatives of ascorbic acid, in particular its phosphate and its salts, erythorbic acid, oligoelements, in particular in the form of a salt, specifically in the form of an aspartate or a chloride of magnesium, selenium, zinc, or copper, alpha-hydroxylated acids, in particular malic acid, lactic acid, and tartaric acid, and esters thereof, in particular with fatty alcohols, such as stearyl alcohol, amino acids, in particular serine, threonine, citrulline, and amino acids constituting NMF (Natural Moisturizing Factor: K. Sakamoto, Cosmet. Toilet. (1984) 99 (3) 109–117), ceramides, in particular 2, 3 or 6 ceramides used singly or in a mixture, photoceramides, in particular those extracted from wheat, and ecdysteroids, in particular ecdysterone, and esters thereof.

In another particular embodiment, said composition is characterized in that the ester of said formula I is used in combination with vitamin A, preferably in the form of an ester such as palmitate.

In a third aspect, the present invention also covers the use as a cosmetic agent of at least one ester of formula I as defined above, advantageously included in the said cosmetic composition.

In the context of its use as a cosmetic agent, the ester of said formula (I) is used to avoid or attenuate the harmful effects of free radicals on the skin, for preventing or treating rashes and sensations of skin prickling or stinging, to favor keratinocyte differentiation, to restore normal moisturizing of the epidermis, to improve skin grain fineness, to slow down or treat the effects of aging on the skin, such as the appearance of wrinkles or loose skin, and to attenuate hyperpigmentation, in particular pigmented spots due to skin aging.

The harmful effects of free radicals include a particularly damaging effect due to free radicals constituted by oxygen, namely peroxidyzing cutaneous substances, in particular the membrane lipids of cells such as keratinocytes. These free radicals constituted by oxygen are in ever increasing concentration in polluted atmospheres because of the combined action of temperature, sunlight, and industrial pollutants, including motor vehicle exhaust gases. These free radicals give rise to accelerated aging of the skin, and the effects thereof can be prevented or treated or attenuated by using the esters of the present invention.

In a fourth aspect, the invention also covers the use of at least one ester of above-defined formula I for making a pharmaceutical composition, in particular a dermatological composition, having activity against radicals, against inflammation, or an anesthetic action on cutaneous nerve endings.

In a variant, said composition comprises 0.001% to 5%, and better 0.01% to 1% by weight of the final composition.

In a fifth aspect, the present invention also covers a cosmetic treatment method characterized in that a cosmetically effective quantity of at least one ester of above-defined formula I is applied topically to the skin of a human being, in particular in the form of a composition containing the ester of said formula I at a concentration lying in the range 0.001% to 5%, and preferably in the range 0.01% to 1% by weight of the final composition.

In a sixth aspect, the present invention also covers a therapeutic treatment method characterized in that a therapeutically effective quantity of at least one ester of above-defined formula I is applied topically to the skin of a human being, in particular in the form of a composition containing the ester of said formula I at a concentration lying in the range 0.001% to 5%, and preferably in the range 0.01% to 1% by weight of the final composition. In the context of this therapeutic application, the invention makes it possible to obtain activity against radicals, against inflammation, or anesthetic action on cutaneous nerve endings.

It can be seen from the above description that compositions of the invention can be formulated in any form that is acceptable for use in cosmetics, dermatology, or pharmacy. In particular, it can be constituted by a cream, a lotion, an emulsion, or indeed a lotion.

The invention is described below in detail with the help of various examples given purely by way of illustration and which therefore do not limit the scope of the invention in any way, and also with reference to the accompanying sole FIGURE.

DESCRIPTION OF THE SOLE ACCOMPANYING FIGURE

The sole accompanying FIGURE is a graph with hydrogen peroxide ($H_2O_2$) concentration as used as a generator of free radicals giving rise to cellular toxicity plotted along the abscissa, which toxicity is possibly combated by DHBT of the invention at the concentration under test, and with the percentage of cell viability plotted up the ordinate, as obtained by the neutral red test on normal human keratinocytes or KHn.

In the examples, the percentages are given by weight, the temperature was ambient temperature, and the pressure was atmospheric pressure, except where stated otherwise. When temperatures are given, they are given in degrees Celsius.

EXAMPLE 1

Synthesizing Esters of 2,5-Dihydroxybenzoic Acid with Alpha-Tocopherol

The reaction is based on causing 2,5-dihydroxybenzoic acid to react with alpha-tocopherol, which leads to esters having said chemical formula I being formed, in which A represents the group:

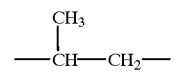

Each of $R_1$, $R_2$ and $R_3$. represents a methyl radical; and $R_4$ and $R_5$ have the above-defined values.

More precisely, synthesis of esters was performed as follows:

A 2 liter flask fitted with half-moon stirring, a thermometer, a cooler, and a Dean Starck apparatus was filled with 172.3 g (0.4 moles) of alpha-tocopherol, 600 g of xylene, and 123.2 g (0.8 moles) of 2,5-dihydroxybenzoic acid.

56 g of 96% sulfuric acid was added at 25° C., thereby producing an exothermal reaction.

The resulting liquid was distilled for a duration of about 7 h. It was cooled to 50° C., about 1000 g were emulsified, and then chloroform extraction was performed by adding 2500 g of chloroform.

The organic phase was washed with 500 g of 2% aqueous solution of sodium carbonate and with 1500 g of water. The mixture was allowed to settle and the aqueous phase separated out.

The chloroform-based organic phase was distilled and 203.4 g of alpha-tocopherol esters were obtained with a yield of 89%. The alpha-tocopherol esters were in the form of a dark brown viscous liquid. When assayed using high performance liquid chromatography (HPLC), from the area ratios, the liquid comprised 6.3% tocopherol, 49% esters of alpha-tocopherol 2,5-dihydroxybenzoate, and 34% other substances.

Method of Purification

A 2 liter flask fitted with half-moon stirring, a thermometer, and a cooler was filled with 180 g of the viscous liquid containing the alpha-tocopherol 2,5-dihydroxybenzoate esters obtained in the preceding step, together with 600 g of toluene, and then active carbon in powder form.

After a period of several hours contact with the active carbon, the liquid was clarified by filtering out the active carbon and the toluene was distilled. This provided 116 g of alpha-tocopherol 2,5-dihydroxybenzoate esters. The yield was 64%. The alpha-tocopherol 2,5-dihydroxybenzoate esters were in the form of a brown viscous liquid.

Further HPLC analysis gave 10.4% alpha-tocopherol, 54% alpha-tocopherol 2,5-dihydroxybenzoate esters, and 31% other substances. This analysis confirmed that the esters were esters of alpha-tocopherol 2,5-dihydroxybenzoate.

It will be observed that this example which is given using alpha-tocopherol can be implemented without difficulty using other tocopherols.

EXAMPLE 2

Preparing Purified Alpha-Tocopherol 2,5-Dihydroxybenzoate Monoester

Alpha-tocopherol 2,5-dihydroxybenzoate monoester can be obtained with good yield by using the synthesis conditions described in Example 1, but by performing a reaction at a lower temperature, of the order of 40° C. to 60° C. and with a shorter reaction time, in the range 2 h to 4 h.

Under such circumstances, the main reaction product obtained is a mixture of alpha-tocopherol 2,5-dihydroxybenzoate diesters and monoester in the form of a chloroform solution, referred to below as SC. These esters can be separated using the following method:

A—Purification of Alpha-Tocopherol 2,5-Dihdroxybenzoate Monoester

From the chloroform solution SC at 100 mg/ml, as obtained above, preparative silica chromatography was carried out, e.g. using a Merck F254 plate, together with a hexane and ethyl acetate mixture (80/20 by volume) as the eluent system. The fraction followed by UV absorption at 320 nm was recovered. It was concentrated and dried. A product having an rf of 0.6 was obtained, constituted by alpha-tocopherol 2,5-dihydroxybenzoate monoester.

The alpha-tocopherol 2,5-dihydroxybenzoate monoester was in the form of a pale beige viscous liquid, that fluoresced under short and long UV, and that was soluble in chloroform and ethanol.

Its empirical chemical formula was $C_{36}H_{54}O_5$ with a molecular weight of 566 g.

Its UV spectrum was characterized by the following $\lambda$ max: 330 nm, 286 nm, 277 nm.

By electron impact mass spectrometry (70 eV), the following $M^+$ characteristic fragments were obtained: 566, 430, 416, 301.

Its developed chemical formula was as follows:

B—A Method of Purifying Alpha-Tocopherol 2,5-Dihydroxybenzoate Diesters

From the said chloroform solution SC at 100 mg/ml, preparative silica chromatography was carried out, e.g. on a Merck F254 plate, using a mixture of hexane and ethyl acetate (20/80 by volume) as the eluant system. A majority fraction followed by UV absorption at 320 nm was recovered and then concentrated and reduced to dryness.

A product having an rf of 0.45 was obtained constituted by a mixture of two alpha-tocopherol 2,5-dihydroxybenzoate diesters, namely: the diester in which the second 2,5-dihydroxybenzoic ester constitutes an ortho substituent of the first ester, referred to as "diester $A_1$" in above-described formula (II), and the diester in which the second 2,5-dihydroxybenzoic ester is a substituent in the meta position of the first ester, referred to as "diester $A_2$" of above-described formula (III).

The characteristics of the mixture of alpha-tocopherol 2,5-dihydroxybenzoic diesters having formulae (II) and (III) respectively are as follows: pale yellow ochre viscous liquid having an rf of 0.45, fluorescent under short and long UV, soluble in chloroform and ethanol. The empirical chemical formula was $C_{43}H_{58}O_8$ with a molecular weight of 702, the UV spectrum presented $\lambda$ max at 338 nm, 286 nm, and 277 nm. Electron impact mass spectrometry (70 eV) gave the following $M^+$ characteristic fragments 702, 670, 662, 647, 566, 430, 416, 301.

By way of example, the diesters $A_1$ and $A_2$ can be separated by subjecting the raw mixture to chromatography on a C-18 silica plate (F254 from MERCK®) using an elution solvent under the following conditions: methanol/water/acetic acid/tetrahydrofuran in the following volume ratio: 88.4/7.6/3.92/0.08.

For the purpose of separating these two diesters by industrial preparative chromatography using a silica column, it is preferable to use as the eluant a 95/5 mixture of hexane and ethyl acetate.

Diester $A_1$ presents the following relative intensities of fragmentation ions close to the molecular ion (702): 702 (10), 670 (70), 662 (14), 647 (22).

Diester $A_2$ presents the following relative intensities of fragmentation ions close to the molecular ion (702): 702 (3), 670 (25), 662 (28), 647 (48).

EXAMPLE 3

Studying the Protective Effect of Alpha-Tocopherol 2,5-Dihydroxybenzoate Esters Against the Cytotoxicity of Free Radicals 1. Principles of the Test Various concentrations of alpha-tocopherol 2,5-dihydroxybenzoate, hereinafter "DHBT", dissolved in dim-

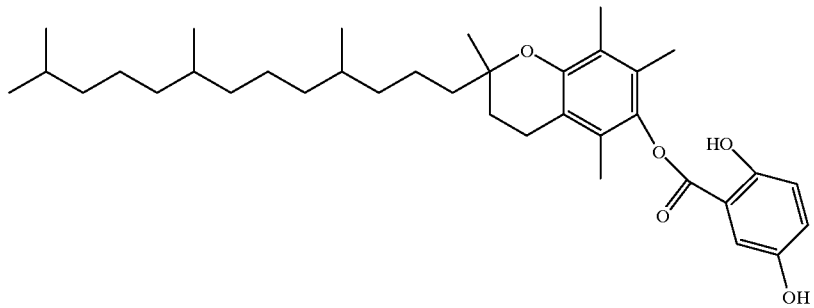

ethylsulfoxide (DMSO) were tested in cultures of normal human keratinocytes (KHn) exposed to various concentrations of oxygen containing free radicals produced by hydrogen peroxide ($H_2O_2$) present in the culture media.

For each concentration tested, cellular viability was evaluated by the so-called "neutral red" test.

The test essentially comprises comparisons, namely:

reference cultures that do not receive hydrogen peroxide, but that do receive DHBT dissolved in DMSO like the treated cultures (control);

cultures that do not receive hydrogen peroxide, and that receive only DMSO, the solvent of DHBT, in quantities identical to that of the cultures treated by DHBT (DMSO reference).

The tested DHBT dissolved in DMSO was in fact the mixture of alpha-tocopherol 2,5-dihydroxybenzoate esters obtained in Example 1.

2. Test Protocol a) Source of the Keratinocytes

Normal human keratinocytes (KHn) that had been taken surgically from healthy skins were used.

b) Culture Conditions

The KHn were maintained in complete serum free media (SFM), referred to below as SFMc, from Gibco. The cells were successively cultivated seven times, and on the seventh pass, referenced P7, the KHn cells were collected.

c) Treatment Conditions

P7 KHn cells were seeded in 96-well culture plates at a rate of 1000 KHn per well in serum free medium, K-SFM medium from Gibco, and treated 24 hours later with various concentrations of hydrogen peroxide ($H_2O_2$, Sigma, reference H-1009), respectively at 1 µM, 5 µM, 10 µM, 25 µM, 50 µM, 75 µM, and 100 µM. For each of these concentrations of $H_2O_2$, three concentrations of tocopherol gentisate were also tested, respectively at 0.1 µg/ml, 1 µg/ml, and 10 µg/ml.

The KHn cells were incubated with the various substances in a HANKS balanced saline solution (HBSS from Gibco, reference: 14175-053) for one hour at 37° C. After incubation, the cells were rinsed with HBSS buffer, and a neutral red test was performed, constituting a viability test, showing up lysosomial activity.

d) Neutral Red Test

This test consisted in rinsing the cells with Dulbecco phosphate buffer (PBS, from Gibco, reference: 14190).

Thereafter, the cells were incubated for 3 hours at 37° C. with 200 µl per well of neutral red solution (mother solution at 0.4% in water) at 1.25% (v/v) in SFMc medium.

Only living cells take on a red color. Consequently, the intensity of the red color, measured in terms of optical density, depends directly on the number of living cells.

After incubation, the cells were rinsed with PBS.

Thereafter, 100 µl were added to each well of a mixture of 50% ethanol+1% acetic acid.

The plate was stirred for 15 minutes.

Thereafter, optical density was measured at 540 nm by spectrophotometry.

Cell viability is expressed in percentage terms, using the following equation:

$$\text{viability}(\%) = \frac{DO_{PH}}{DO_{TB}} \times 100$$

in which, for each value of DHBT concentration, $DO_{TB}$ is the optical density of "control" cultures, and $DO_{PH}$ is the optical density of cultures containing hydrogen peroxide ($H_2O_2$).

3. Results

The results obtained are summarized in Table I below.

TABLE I

Viability (%) of $KH_n$ keratinocytes in culture, in the presence of alpha-tocopherol 2,5-dihydroxybenzoate (DHBT) and oxygen-containing free radicals

|  | NO DHBT Mean | σ | DHBT 0.1 µg/ml Mean | σ | DHBT 1 µg/ml Mean | σ | DHBT 10 µg/ml Mean | σ |
|---|---|---|---|---|---|---|---|---|
| Control | 100.00 | 6.82 | 100 | 2.82 | 100 | 2.45 | 100 | 4.21 |
| DMSO reference |  |  | 107.38** | 1.11 | 103.85** | 1.04 | 105.31** | 3 |
| $H_2O_2$ 1 µm | 108.25 | 8.13 | 110.47 | 3.66 | 99.88 | 1.36 | 103.67 | 3.66 |
| $H_2O_2$ 5 µm | 106.93 | 6.2 | 109.88 | 0.45 | 106.87 | 0.67 | 107.67 | 3.11 |
| $H_2O_2$ 10 µm | 109.04 | 8.44 | 102.85 | 8.47 | 103.74 | 2.26 | 111.99 | 2.44 |
| $H_2O_2$ 25 µm | 95.16 | 6.39 | 94.16 | 20.07 | 99.21 | 4.49 | 112.35 | 4.59 |
| $H_2O_2$ 50 µm | 85.33* | 4.74 | 85.1* | 2.75 | 86.52* | 4.32 | 107.04 | 4.93 |
| $H_2O_2$ 75 µm | 72.42* | 11.4 | 85.37* | 2.65 | 72.46* | 3.32 | 90.73* | 4.41 |
| $H_2O_2$ 100 µm | 59.07* | 8.9 | 68.4* | 4.08 | 53.04* | 6.87 | 85.71* | 2.43 |

*Results significant at 5% ($p < 0.05$).
**DMSO reference cultures did not receive DHBT, but only DMSO.

The same results are also plotted as curves in the sole accompanying FIGURE.

The concentrations of hydrogen peroxide ($H_2O_2$) used as a generator of free radicals giving rise to cellular toxicity is plotted along the abscissa, and is possibly combated by the DHBT of the invention at the concentration under test, while the cell viability percentage is plotted up the ordinate, as obtained by the neutral red test on normal human keratinocytes or KHn.

The curve interconnecting circles corresponds to cultures containing hydrogen peroxide, but not receiving DHBT; the curve connecting squares corresponds to cultures receiving DHBT in DMSO of the invention at a concentration of 0.1 µg/ml of culture; the curve connecting triangles corresponds to cultures receiving DHBT in DMSO of the invention at a concentration of 1 µg/ml of culture, and finally the curve connecting crosses corresponds to cultures receiving DHBT of the invention at a concentration of 10 µg/ml of culture.

It is recalled that cultures corresponding to the DMSO reference did not receive DHBT, but only its solvent DMSO.

From Table I, and from the curves plotted in the sole accompanying FIGURE, it can be seen that hydrogen peroxide is toxic for the keratinocytes used as from 25 µM, above which the cell viability rate drops sharply from about 100%.

However, when the cells are treated both with hydrogen peroxide and with DHBT of the invention at a concentration of 10 μg/ml, the toxicity of the hydrogen peroxide is not observable until its concentration is 75 μM, i.e. until its concentration is three times greater, which demonstrates significant resistance of the keratinocytes to attack from free radicals, with this being achieved by DHBT at such a concentration.

Thus, this test shows clearly that the antiradical activity is particularly effective, specifically for making a pharmaceutical composition, in particular a dermatological composition, or a cosmetic composition, or as a cosmetic agent.

In addition, given that the oxygen-containing free radicals peroxidize cutaneous lipids, the present invention makes it possible to prevent or treat effectively the effects of aging on the skin. In particular, those effects which are due to free radicals, and specifically those which are generated by atmospheric pollution.

The invention is described below with reference to various examples of cosmetic or pharmaceutical, in particular dermatological compositions given merely as illustrations and which therefore do not limit the scope of the invention in any way.

In the examples, concentrations are given in grams.

EXAMPLE 4

Antiwrinkle Cream

| The cream was prepared using the following active ingredients: | |
|---|---:|
| purified tocopherol esters of Example 1 | 0.1 g |
| jojoba oil | 2 g |
| sesame oil | 3 g |
| vitamin A in palmitate form | 0.01 g |
| glycerol | 2 g |
| water + preservative + surfactant + scent | qsp 100 g |

The cream was prepared as follows. The tocopherol esters were initially dissolved in the jojoba oil and the sesame oil mixed together, and then the palmitate of vitamin A and the glycerol were added, and finally the aqueous phase with the surfactant system was added and the mixture stirred until it was homogenous.

This produced a cream which, when applied in the evening for several weeks, refined skin grain, gave a luminous complexion, and countered the appearance of wrinkles.

EXAMPLE 5

Anti-Aging Composition in the Form of an Emulsion

| The composition was prepared from the following active ingredients: | |
|---|---:|
| the mixture of tocopherol 2,5-dihydroxybenzoate diesters prepared in Example 2 | 0.025 g |
| stearates of polyethylene glycol 6 and polyethyleneglycol 32 as commercially available under the trade reference TEFOSE 63 ® | 15 g |
| cetyl palmitate | 3 g |
| cetyl alcohol | 3 g |
| 2-hexyl-1-dodecanol | 5 g |
| glycerin | 3 g |

| -continued | |
|---|---:|
| The composition was prepared from the following active ingredients: | |
| 2% Carbopol 980 ® gel | 5 g |
| purified water + preservative + scent | qsp 100 g |

To prepare the emulsion, the mixture of tocopherol 2,5-dihydroxybenzoate diesters was initially mixed with the fatty phase until it had been completely dissolved, said fatty phase being constituted by the glycerin, the stearates of polyethyleneglycol, the cetyl palmitate, the cetyl alcohol, and the octyldodecanol. Thereafter the purified water was added under stirring to form an emulsion, and the carbopol gel was added to gel the emulsion.

An emulsion- or cream-forming composition was obtained that was applied locally for several weeks as an anti-aging care cream.

EXAMPLE 6

Composition in the Form of a Dermatological Lotion

| The dermatological composition was obtained from the following active ingredients: | |
|---|---:|
| the mixture of tocopherol 2,5-dihydroxybenzoate diesters as obtained in Example 2 | 0.5 g |
| absolute ethanol | 35 g |
| scented purified water | qsp 100 g |

The composition was prepared by initially mixing the diesters in the absolute ethanol, after which the purified water was added under stirring so as to constitute said lotion.

The lotion as applied on the skin presented anti-aging action, refined skin grain, and gave it a luminous complexion.

What is claimed is:

1. Esters, characterized in that they present the following chemical formula (I):

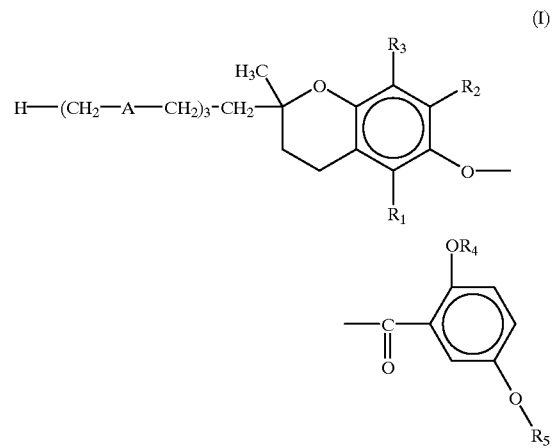

in which:

$R_1$, $R_2$ and $R_3$ independently represent an atom of hydrogen, a methyl radical, A represents the following groups:

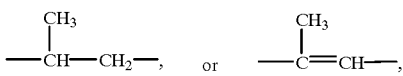

$R_4$ and $R_5$ are identical or different and each represents a chain of the form:

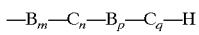

in which:
B is the following group:

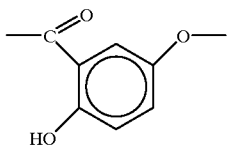

C is the following group:

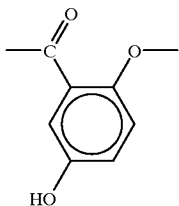

and in which the indices m, n, p, and q are respective integers lying in the range 0 to 4, it being understood that the sum m+n+p+q is limited to integers in the range 0 to 4.

2. Esters according to claim 1, characterized in that $R_4$ and $R_5$ represent hydrogen.

3. Esters according to claim 1, characterized in that at least one of the groups $R_4$ and $R_5$ represents hydrogen.

4. Esters according to claim 3, characterized in that one of the groups $R_4$ or $R_5$ represents hydrogen, and the other a 2,5-dihydroxybenzoyl radical.

5. Esters according to claim 1, characterized in that they are selected from the group consisting in esters of alpha-tocopherol, of beta-tocopherol, of gamma-tocopherol, of zeta 1-tocopherol, of zeta 2-tocopherol, of delta-tocopherol, of eta-tocopherol, of epsilon-tocopherol, and of tocol.

6. An ester satisfying following formula (II):

7. A composition selected from the group consisting of a cosmetic and a pharmaceutical composition comprising as an active ingredient at least one ester as defined in claim 1, optionally in a cosmetically or pharmaceutically acceptable excipient.

8. The composition of claim 7, comprising as an active ingredient at least two esters defined in claim 1, in the form of a mixture.

9. The composition of claim 7, having a fatty phase comprising at least one cosmetically or pharmaceutically acceptable oil selected from the group consisting of jojoba oil, macadamia oil, limnanthes seed oil, a mineral oil, a triglyceride, and mixtures thereof.

10. The composition of claim 9, wherein said limnanthes seed oil is *Limnanthes alba benth* seed oil; said triglycerides comprising an acid selected from caprylic acid, capric acid and mixtures thereof.

11. The composition of claim 7, wherein the ester concentration ranges between 0.001% and 5% by weight relative to the total weight of the final composition.

12. The composition of claim 7, wherein the ester concentration ranges between 0.1% and 5% by weight with respect to the total weight of the final composition.

13. The composition of claim 7, wherein the ester concentration ranges between 0.1% and 1% by weight relative to the total weight of the final composition.

14. The composition of claim 7, comprising as an active ingredient at least one alpha-tocopherol ester of chemical formula I as defined in claim 1, in which each of $R_1$, $R_2$ and $R_3$ represents a methyl radical and A represents the group:

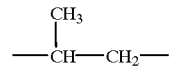

and $R_4$ and $R_5$ are as defined in claim 1.

15. The composition of claim 7, further comprising at least one other active ingredient selected from the group consisting of a vitamin, retinoic acid, retinal, retinol, a retinoic acid ester, a retinal ester, a retinol ester, salicylic acid, a salicylic acid salt, a salicylic acid ester, 2,5-dihydroxybenzoic acid, tocopherol, a tocopherol ester, asiatic acid, madecassic acid, an ester of asiatic acid with a glycoside, an ester of madecassic acid with a glycoside, asiaticoside, an extract of *Centella asiatica*, an extract of *Siegesbeckia orientalis*, a proantocyanide oligomer, an ester of proantocyanide oligomer, a salt of ascorbic acid, ascorbic phosphate, erythorbic acid, a trace element, a trace element salt, an alpha-hydroxylated acid, an ester of alpha-

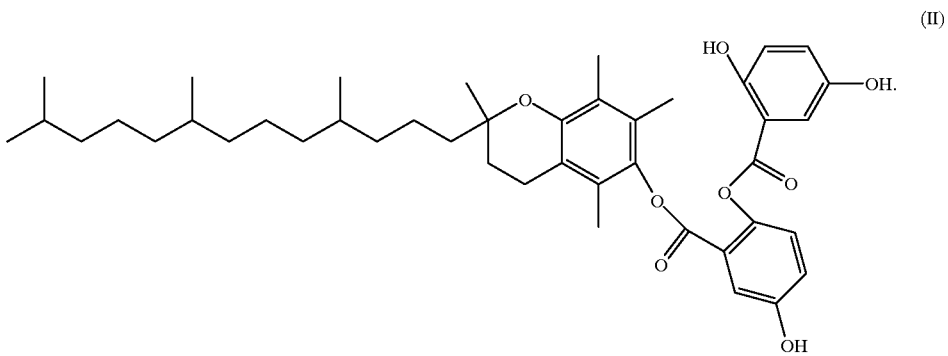

hydroxylated acid, an amino acid, an amino acid constituting NMF, a ceramide, a photoceramide, an ecdysteroid, an ecdysteroid ester, and mixtures thereof.

16. The composition of claim 7, wherein said ester is used in admixture with vitamin A or an ester of vitamin A.

17. The composition of claim 16, wherein said vitamin A ester is vitamin A palmitate.

18. A method of cosmetic skin care comprising delivering topically to the skin of a human being a cosmetically effective amount of at least one ester as defined in claim 1.

19. A method of cosmetic care for performing a cosmetic care selected from the group consisting of avoiding or lowering the harmful effects of free radicals on the skin, for slowing down or eliminating rashes or sensations of skin prickling or stinging, of favoring keratinocyte differentiation, of restoring normal moisturizing of the epidermis, of improving skin grain fineness, of slowing down or treating the effects of aging on the skin, of attenuating hyperpigmentation, comprising delivering topically to skin areas of a human being in need thereof, of a cosmetically effective amount of at least one ester defined in claim 1.

20. The cosmetic method of claim 19, wherein said ester is present in a composition containing said ester at a concentration ranging between 0.001% and 5% by weight of the final composition.

21. A method of performing a therapeutic treatment of a human being in need thereof, said therapeutic treatment being selected from the group consisting of counteracting free radicals, counteracting skin inflammation, having an anesthetic action on cutaneous nerve endings of the skin, comprising topically delivering to skin areas of said human being in need thereof, of a therapeutically effective amount of an ester as defined in claim 1.

22. The method of claim 21, wherein said ester is present in a pharmaceutical composition at a concentration ranging between 0.001% and 5% by weight of the final therapeutic composition.

* * * * *